(12) United States Patent
Sun (10) Patent No.: US 7,652,149 B2
(45) Date of Patent: Jan. 26, 2010

(54) CRYSTALLINE PYRAZOLES

(75) Inventor: Changquan Sun, Portage, MI (US)

(73) Assignee: Pharmacia & Upjohn Company LLC, Kalamazoo, MI (US)

( * ) Notice: Subject to any disclaimer, the term of this patent is extended or adjusted under 35 U.S.C. 154(b) by 548 days.

(21) Appl. No.: 11/095,381

(22) Filed: Mar. 31, 2005

(65) Prior Publication Data

US 2005/0222240 A1   Oct. 6, 2005

Related U.S. Application Data (60) Provisional application No. 60/558,469, filed on Apr. 1, 2004.

(51) Int. Cl.
    *C07D 207/00*   (2006.01)
(52) U.S. Cl. .................................. 548/373.1
(58) Field of Classification Search ............... 548/373.1
    See application file for complete search history.

(56) References Cited

U.S. PATENT DOCUMENTS

| | | | |
|---|---|---|---|
| 5,314,506 A | 5/1994 | Midler, Jr. et al. | |
| 5,466,823 A | 11/1995 | Talley | |
| 5,521,207 A * | 5/1996 | Graneto | 514/406 |
| 6,045,773 A | 4/2000 | Isakson et al. | |
| 6,083,986 A | 7/2000 | Castle et al. | |
| 6,221,153 B1 | 4/2001 | Castor et al. | |
| 6,492,411 B1 | 12/2002 | Talley | |
| 6,787,154 B2 | 9/2004 | Albani | |

FOREIGN PATENT DOCUMENTS

| EP | 1167355 | 1/2002 |
|---|---|---|
| WO | 0032189 A1 | 6/2000 |

OTHER PUBLICATIONS

Brittain, et al., Polymorphism in Pharmaceutical, vol. 95, 1999, pp. 348-361.*
Threlfall, T.L., "Analysis of Organic Polymorphs, A Review," Analyst, vol. 120, pp. 2435-2459.

* cited by examiner

*Primary Examiner*—Golam M. M. Shameem
*Assistant Examiner*—Susannah Chung
(74) *Attorney, Agent, or Firm*—Timothy J. Gumbleton; Martha A. Gammill (57) ABSTRACT

The present invention relates to crystal forms of 4-[5-(4-fluorophenyl)-3-(trifluoromethyl)-1H-pyrazol-1-yl]-benzenesulfonamide and methods for preparation, interconversion, and isolation of such crystals.

1 Claim, 4 Drawing Sheets

CRYSTALLINE PYRAZOLES

CROSS REFERENCE

This application claims benefit of U.S. Provisional Patent Application Ser. No. 60/558,469, filed Apr. 1, 2004.

FIELD OF THE INVENTION

The present invention relates to crystal forms of 4-[5-(4-fluorophenyl)-3-(trifluoromethyl)-1H-pyrazol-1-yl]-benzenesulfonamide and methods for preparation, interconversion, and isolation of such crystals.

BACKGROUND OF THE INVENTION

1. Field of Invention

5-Phenylpyrazolyl-1-benzenesulfonamides are a novel synthetic class of compounds with potent COX-2 inhibitory activity useful for the treatment of arthritis and other conditions due to inflammation. 4-[5-(4-fluorophenyl)-3-(trifluoromethyl)-1H-pyrazol-1-yl]-benzenesulfonamide is a 5-phenylpyrazolyl-1-benzenesulfonamide having the following structure:

Formula I

2. Background Art

The compound of Formula I is disclosed in U.S. Pat. No. 5,466,823 (Tally et al.) and U.S. Pat. No. 5,521,207 (Graneto). These patents are incorporated herein by reference. Although the preparation of the compound of Formula I is disclosed, the specification is silent as to the isolation and nature of crystal forms of the agent. There is a need to identify polymorphic behavior as a means of ensuring robust processes, avoid tableting problems, tablet failure, crystal growth in suspensions and resultant caking, precipitation from suspensions as well as chemical production problems such as filterability, and to ensure analytical reproducibility (see *Analysis of Organic Polymorphs, A Review*; Threlfall, T. L., Analyst, 120, pp. 2435-2459).

SUMMARY OF THE INVENTION

In one aspect, the present invention provides a crystal, Form I, of 4-[5-(4-fluorophenyl)-3-(trifluoromethyl)-1H-pyrazol-1-yl]-benzenesulfonamide having a powder X-ray diffraction pattern comprising peaks expressed in degrees (±0.1 degree) of two theta angle of 14.0, 18.9, 21.3, 21.9, and 25.7 obtained using CuKα$_1$ X-ray (wavelength=1.5406 Angstroms). In another aspect of the invention, a process is provided for converting crystal Form II of 4-[5-(4-fluorophenyl)-3-(trifluoromethyl)-1H-pyrazol-1-yl]-benzenesulfonamide into the crystal Form I comprising i) mixing a suspension of Form II of 4-[5-(4-fluorophenyl)-3-(trifluoromethyl)-1H-pyrazol-1-yl]-benzenesulfonamide in a suitable solvent at a temperature from about 0° C. to about 60° C.; ii) stirring the suspension at a temperature from about 0° C. to about 60° C. for 24 to 72 hours; and iii) collecting the Form I crystals. In another aspect of the invention, the solvent in said process is chosen from the group consisting of water, methanol, ethanol, isopropanol, acetone, acetonitrile, methylene chloride, toluene, and tetrahydrofuran, and mixtures thereof.

An additional aspect of the invention is process for converting crystal Form II of 4-[5-(4-fluorophenyl)-3-(trifluoromethyl)-1H-pyrazol-1-yl]-benzenesulfonamide into the crystal Form I comprising (i) dissolving said Form II in a water miscible solvent in which the solubility of Form II is greater than 2 mg/mL at a temperature from about 10° C. to about 60° C.; (ii) precipitating the compound by the addition of water; (iii) stirring the suspension of step (ii) for 2 to 72 hours at a temperature from about 15° C. to about 45° C.; and (iv) collecting the Form I crystals. In another aspect of the invention, solvent for this process is selected from the group consisting of ethanol, acetone, acetonitrile, tetrahydrofuran, dioxane, and dimethylformamide.

In a further aspect, the invention provides a pharmaceutical composition which comprises a compound of Formula I of crystal Form I. In another aspect of the invention, the pharmaceutical composition further comprises a pharmaceutically acceptable carrier or excipient. Still another object of the present invention is to provide a method for preventing or treating inflammatory conditions in animals by using a therapeutically effective amount of a novel composition of the present invention. A further object of the present invention is to provide a use of a novel composition of the present invention in the manufacture of a medicament for the prevention or treatment of an inflammatory condition in an animal.

A further object of the invention is to prepare crystal Form I of 4-[5-(4-fluorophenyl)-3-(trifluoromethyl)-1H-pyrazol-1-yl]-benzenesulfonamide by:

Step (a) mixing 1.0 to 1.6 moles, or preferably 1.2 to 1.45 moles, or more preferably 1.25 to 1.35 moles, of alkyl trifluoroacetate per mole of 4-fluoroacetophenone with 1.0 to 1.5 moles, or preferably 1.1 to 1.35 moles, or more preferably 1.15 to 1.25 moles, of a metal alkoxide per mole of 4-fluoroacetophenone, and a known quantity of 4-fluoroacetophenone to make a mixture. Optionally, up to 1,380 ml, or preferably up to 900 ml, or more preferably up to 490 ml, of a suitable solvent, preferably 2-propanol, is added in this step. Optionally, the mixture of step (a) is heated at a temperature above ambient temperature up to reflux temperature, or preferably at a temperature of 40° C. to 70° C., or more preferably at a temperature of 50° C. to 60° C., for 1 to 24 hours, or preferably for 1 to 10 hours; or more preferably for 1 to 4 hours, or more preferably until the reaction is complete. Optionally, after such heating, the mixture is then cooled to a temperature of −5° C. to 30° C., or more preferably to ambient temperature.

Step (b) The mixture of step (a) is combined with, or preferably added to, a combination of 415 to 1,245 ml, or preferably 650 to 870 ml, or more preferably 725 to 795 ml, of water per mole of 4-fluoroacetophenone, plus 1.1 to 2.0 moles, or preferably 1.2 to 1.7 moles, or more preferably 1.3 to 1.5 moles, of concentrated hydrochloric acid per mole of 4-fluoroacetophenone, plus 0.8 to 1.2 moles, or preferably 0.9 to 1.1 moles, or more preferably 0.95 to 1.05 moles, of 4-sulfonamidophenylhydrazine hydrochloride per mole of 4-fluoroacetophenone, and an amount of a suitable solvent, preferably a $C_1$-$C_6$ alcohol, or more preferably 2-propanol, so that the total amount of the solvent in the mixture is from 550 to 1,660 ml, or preferably from 600 to 1,000 ml, or more preferably from 650 to 750 ml, per mole of 4-fluoroacetophenone. Optionally, the mixture of step (b) is heated at a temperature above ambient temperature up to reflux temperature, or preferably at a temperature of 40° C. to 70° C., or preferably at a temperature of 50° C. to 70° C., for 1 to 24 hours, or preferably for 1 to 10 hours; or more preferably for 1 to 4 hours, or more preferably until the reaction is complete. Optionally, after such heating, the mixture is then stabilized at a temperature of ambient temperature to 70° C., or preferably from 40° C. to 65° C., or more preferably from 50° C. to 60° C.

Step (c) Then, a seeding amount, or preferably 0.0001% to 50% wt/wt, or more preferably 0.001% to 5% wt/wt, or more preferably 0.01% to 0.5% wt/wt, of crystals of Form I of 4-[5-(4-fluorophenyl)-3-(trifluoromethyl)-1H-pyrazol-1-yl]-benzenesulfonamide relative to 4-fluoroacetophenone is added to the mixture. Optionally, the mixture of step (c) is heated at a temperature from 40° C. to less than 70° C., or preferably at a temperature of 50° C. to less than 70° C., or more preferably at a temperature of 50° C. to 60° C., for 1 to 10 hours, or preferably for 3 to 8 hours; or more preferably for 5 to 7 hours. Optionally, after such heating, the mixture is then cooled to a temperature of −5° C. to 30° C., or more preferably to ambient temperature. Optionally, the mixture is filtered and washed with a suitable solvent, preferably an alcohol, more preferably 2-propanol, or water or a mixture thereof. Optionally, the solvent is in an amount of 300 to 1,500 ml, or preferably 600 to 1060 ml, or more preferably 800 to 860 ml, of per mole of 4-fluoroacetophenone, and the water is in an amount of 100 to 700 ml, or preferably 285 to 545 ml, or more preferably 385 to 445 ml, per mole of 4-fluoroacetophenone.

Step (d) The Form I crystals are then collected. Optionally, the Form I crystals are dried at a temperature of 15° C. to 80° C., or preferably at a temperature of 30° C. to 65° C., more preferably at 50° C. to 60° C.

In another aspect of the invention, the metal alkoxide of step (a) is chosen from the group consisting of sodium methoxide, sodium ethoxide, sodium isopropoxide, sodium tertiary butoxide, lithium methoxide, lithium ethoxide, lithium isopropoxide, lithium tertiary butoxide, potassium methoxide, potassium ethoxide, potassium isopropoxide, and potassium tertiary butoxide, and mixtures thereof, or preferably sodium methoxide.

These, and other objects, will readily be apparent to those skilled in the art.

DETAILED DESCRIPTION OF THE INVENTION

The selective COX-2 inhibitor 4-[5-(4-fluorophenyl)-3-(trifluoromethyl)-1H-pyrazol-1-yl]-benzenesulfonamide (Formula I)

Formula I has been described in U.S. Pat. Nos. 5,466,823 and 5,521,207. The description describes a synthesis of the compound, but is silent with respect to the crystalline form which is obtained. As described in the examples, following the procedure given in these patents leads to crystals of Form II, which has been demonstrated by powder X-ray diffraction (PXRD) patterns. The inventors have found that this crystal form is unstable with respect to another form, Form I, at ambient temperature and pressure. The forms can be distinguished by their PXRD (powder X-ray diffraction) patterns.

Definitions

As referred to in the present application, "water miscible" means capable of being mixed with or dissolved in water at all proportions.

As referred to in the present application, "anhydrous crystalline" refers to a crystal that does not contain substantial amounts of water. The water content can be determined by methods known in the art including, for example, Karl Fischer titrations. Preferably an anhydrous crystalline form contains at most about 1% by weight water, more preferably at most about 0.5% by weight water, and most preferably at most about 0.1% by weight water.

As referred to in the present application, "stable" in bulk drug stability tests means that at least about 90% by weight, preferably at least about 95% by weight, and more preferably at least about 99% by weight of the bulk drug remains unchanged after storage under the indicated conditions for the indicated time.

"DSC" means differential scanning calorimetry.

The term alkyl, unless otherwise specified, where used either alone or with other terms such as "trifluoroacetate", embraces linear or branched having one to four carbon atoms, or preferably two carbon atoms. Non-limiting examples include groups such as methyl, ethyl, n-propyl, isopropyl, n-butyl, t-butyl, isobutyl, and sec-butyl.

"Metal alkoxides" are metal salts of an alcohol. Generally, the metal alkoxides contain sodium, lithium, or potassium as the metal. In this invention they are used in the form of an alcohol solution. Generally, the alcohol corresponds to the alcohol of the alkoxide. Non-limiting examples of metal alkoxides include sodium methoxide, sodium ethoxide, sodium isopropoxide, sodium tertiary butoxide, lithium methoxide, lithium ethoxide, lithium isopropoxide, lithium tertiary butoxide, potassium methoxide, potassium ethoxide, potassium isopropoxide, potassium tertiary butoxide, and mixtures thereof.

Seeding is a technique of using a single crystal or more to induce the formation of more crystals from a mixture, solution, or suspension. A seeding amount is the amount of material that, when added to a mixture, solution, or suspension, is able to cause the formation of the desired form of a compound. While in theory, this amount can be very small, in practice, a larger amount is used. This amount can be any amount that can be reasonably handled and is sufficient to cause the formation of the desired form of a compound. As a non-limiting example, amounts of 0.0001% to 50% wt/wt of the seeding compound based on a reference compound can be used as a seeding amount.

The term "C" when used in reference to temperature means centigrade or Celsius.

"Ambient temperature" is the air temperature surrounding an object. It is the temperature inside a room, which generally is from 15 to 25 degrees centigrade.

Reflux is a technique used in chemistry to apply energy to reactions over an extended period of time. For this technique, a liquid reaction mixture is placed in a vessel open only at the top. This vessel is connected to a vertical condenser, such that any vapors given off are cooled back to liquid, and fall back into the reaction vessel. The vessel is then heated vigorously for the course of the reaction. The advantage of this technique is that it can be left for a long period of time without the need to add more solvent or fear of the reaction vessel boiling dry. In addition because a given solvent will always boil at a certain temperature, the reaction will proceed at the same temperature. Because different solvents boil at different temperatures, by careful choice of solvent, the temperature of the reaction can be controlled. "Reflux temperature" as used herein refers to the temperature at which a particular solvent boils during the reflux technique. For example, 2-propanol has a boiling point of 82° C.; methanol has a boiling point of 65° C. at sea level.

In reference to step (a), "reaction completion" is determined by confirming that the amount of 4-fluoroacetophenone left in the mixture is less than or equal to 2% w/w relative to the input charge of 4-fluoroacetophenone by using the following HPLC method:

| Column: Discover HS F5, 5 u, 250 × 4.6 mm Supelco Cat # 567517-U Mobile Phase (Gradient): | | |
| --- | --- | --- |
| Time | % Mobile Phase A | % Mobile Phase B |
| 0 | 60 | 40 |
| 15.0 | 60 | 40 |
| 15.1 | 20 | 80 |
| 20.0 | 20 | 80 |
| 20.1 | 60 | 40 |
| 27.0 | 60 | 40 |

| | |
| --- | --- |
| A: | 0.05% (v/v) TFA in Water |
| B: | 0.05% (v/v) TFA in Acetonitrile |
| Flow Rate: | 1 ml/min |
| Injection: | 20 µl |
| Detection: | 247 nm |

In reference to step (b), "reaction completion" is determined by confirming that the amount of 4-[5-(4-fluorophenyl)-3-(trifluoromethyl)-1H-pyrazol-1-yl]-benzenesulfonamide formed is greater than 90% by using the following HPLC method:

| | |
| --- | --- |
| Column: | Zorbax Eclipse XDB Phenyl, 3.5 µm, 150 × 4.6 mm |
| Mobile Phase: | 55/45 v/v Methanol/25 mM $H_3PO_4$ at pH 2.5 (pH adjusted with NaOH) |
| Run time: | 30 mins |
| Column temperature: | 35° C. |
| Flow rate: | 1.0 ml/min |
| Injection volume: | 15 µl |
| Detection: | UV at 254 nm |
| Sample concentration: | 0.4 mg/ml |

"Therapeutically effective amount" refers to that amount of the compound being administered which will prevent a condition (eg, an inflammatory condition), or will relieve to some extent one or more of the symptoms of the disorder being treated. Pharmaceutical compositions suitable for use in the present invention include compositions wherein the active ingredients are contained in an amount sufficient to achieve the intended purpose. Determination of a therapeutically effective amount is well within the capability of those skilled in the art, especially in light of the detailed disclosure provided herein.

Animals that are suitable recipients of the compounds of the present invention include but are not limited to humans or other mammals or animals, for example, farm animals including cattle, sheep, pigs, horses, goats and poultry (e.g., chickens, turkeys, ducks and geese) and other birds, and companion animals such as dogs, cats, and exotic and/or zoo animals. Treatment of both rodents and non-rodent animals is contemplated.

In practice, the amount of the compound to be administered ranges from about 0.001 to 100 mg per kg of animal body weight, such total dose being given at one time or in divided doses. It may be administered alone or in combination with one or more other drugs. Generally, it will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

For use as an anti-inflammatory agent in animals the inventive composition may be administered either orally or by injection. Where it is desired to administer the inventive composition in a dry, solid unit dosage form, capsules, boluses or tablets containing the desired amount of active compounds usually are employed. These dosage forms are prepared by intimately and uniformly mixing the active ingredient with suitable finely divided diluents such as starch, lactose, talc, magnesium stearate, vegetable gums, and the like. Such unit dosage formulations may be varied widely with respect to their total weight and content of the anti-inflammatory agent depending upon factors such as the type of host animal to be treated, the severity and type of inflammation, and the weight of the host. The formulation of tablets is discussed in *Pharmaceutical Dosage Forms: Tablets*, Vol. 1, by H. Lieberman and L. Lachman (Marcel Dekker, New York, 1980).

Alternatively, the anti-inflammatory compositions of the present invention may be administered to animals parenterally, for example, by intraruminal, intramuscular, or subcutaneous injection in which event the active ingredients are dissolved or dispersed in a liquid carrier vehicle. For parenteral administration, the active materials are suitably admixed with an acceptable vehicle, preferably of the vegetable oil variety such as peanut oil, cottonseed oil, and the like. Other parenteral vehicles such as organic preparations using solketal, propylene glycol, glycerol formal, and aqueous parenteral formulations are also used, often in combination in various proportions. The active compound or compounds are dissolved or suspended in the parenteral formulation for administration; such formulations generally contain from 0.005 to 5% by weight of the active compound.

DETAILED DESCRIPTION OF THE INVENTION

In the following description of the invention, specific embodiments in which the invention may be practiced are described. These embodiments are described in sufficient detail to enable those skilled in the art to practice the invention. Other embodiments may be utilized, and logical and other changes may be made without departing from the scope of the invention. The following detailed description is, therefore, not to be taken in a limiting sense, and the scope of the invention is defined only by the appended claims, along with the full scope of equivalents to which such claims are entitled.

Form II is the crystal form obtained from the procedure described in U.S. Pat. No. 5,466,823. Methods for obtaining crystal Form I are illustrated by the following non-limiting descriptions and examples.

In one method, 4-[5-(4-fluorophenyl)-3-(trifluoromethyl)-1H-pyrazol-1-yl]-benzenesulfonamide of crystal Form II may be suspended and mixed in suitable solvent in which the concentration of drug is higher than the saturation point, at a temperature from about 0° C. to about 60° C. A suitable solvent is one in which the solubility of the drug is greater than about 1 mg/mL and less than about 800 mg/mL. Examples of suitable solvents include but are not limited to water, methanol, ethanol, isopropanol, acetone, acetonitrile, methylene chloride, toluene, and tetrahydrofuran, and mixtures thereof. The suspension is stirred at a temperature from about 0° C. to about 60° C. for 24 to 72 hours. The Form I crystals are collected by filtration.

In another procedure, the crystal Form I can be prepared by precipitation from a solution of 4-[5-(4-fluorophenyl)-3-(trifluoromethyl)-1H-pyrazol-1-yl]-benzenesulfonamide in a suitable water miscible solvent in which the compound solubility is greater than 2 mg/mL, by the addition of water at a temperature from about 10° C. to about 60° C. Examples of suitable solvents for the preparation of Form I from Form II include ethanol, acetone, acetonitrile, tetrahydrofuran, dioxane, and dimethylformamide. Subsequent to the initial precipitation with water, the suspension is stirred for 24 to 72 hours at a temperature from about 15° C. to about 45° C., and the Form I crystals are collected by filtration.

Preparation 1. Preparation of 4-[5-(4-fluorophenyl)-3-(trifluoromethyl)-1H-pyrazol-1-yl]-benzenesulfonamide, Form II The following procedure is essentially identical to that of Example 1 of U.S. Pat. No. 5,521,207 with the non-critical variation of using 4-fluroacetophenone instead of 4-chloroacetophenone as a starting material.

Step 1: Preparation of 4,4,4-trifluoro-1-[4-(fluoro)phenyl]-butane-1,3-dione

Ethyl trifluoroacetate (2.35 g, 1.66 mmol) was placed in a 50 mL round bottom flask, and dissolved in methyl tert-butyl ether (7.5 mL). To the stirred solution was added 25 weight % sodium methoxide (4.0 mL, 17.7 mmol) via an addition funnel over a 2 minute period. Next, 4'-fluoroacetophenone (2.1 g, 15 mmol) was dissolved in methyl tert-butyl ether (2 mL), and added to the reaction dropwise over 5 minutes. After stirring overnight (15.75 hours), 3N HCl (7.0 mL) was added. The organic layer was collected, washed with brine (7.5 mL), dried over $MgSO_4$, filtered, and concentrated in vacuo to give 3.2 g of pale-orange solid. The solid was recrystallized from iso-octane to give 2.05 g of the dione.

Step 2: Preparation of 4-[5-(4-fluorophenyl)-3-(trifluoromethyl)-1H-pyrazol-1-yl]-benzenesulfonamide 4-Sulphonamidophenyl hydrazine hydrochloride (982 mg, 4.4 mmol) was added to a stirred solution of 4,4,4-trifluoro-1-[4-(fluoro)phenyl]-butane-1,3-dione (0.936 g, 4.0 mmol) in ethanol (50 mL). The reaction was heated to reflux and stirred for 20 hours. After cooling to room temperature, the reaction mixture was concentrated in vacuo. The residue was taken up in ethyl acetate and washed with water and brine and dried over $MgSO_4$, filtered, and concentrated in vacuo to give a brown solid which was recrystallized from ethyl acetate and iso-octane to give the 4-[5-(4-fluorophenyl)-3-(trifluoromethyl)-1H-pyrazol-1-yl]-benzenesulfonamide, 0.8 g.

hu 1H NMR ($CDCl_3$): δ 7.92, 7.47, 7.22, 7.09, 6.76, 4.92.

MS m/e ES-(M−H) 384 m.p. 167-171° C.

Preparation 2. Preparation of 4-[5-(4-fluorophenyl)-3-(trifluoromethyl)-1H-pyrazol-1-yl]-benzenesulfonamide, Form I Without Isolating the Crystal Form II The following procedure describes a general method of preparing the crystal Form I of 4-[5-(4-fluorophenyl)-3-(trifluoromethyl)-1H-pyrazol-1-yl]-benzenesulfonamide without isolating the crystal Form II.

Part A. 4-fluoroacetophenone (1 molar equivalent) is combined with a mixture of alkyl trifluoroacetate (1.0-1.6 molar equivalents), a metal alkoxide (1.0-1.5 molar equivalents) and optionally a suitable solvent (up to 10 liters per kilogram of 4-fluoroacetophenone). This mixture may be heated at temperatures of up to reflux (to effect completion of reaction). A "suitable solvent" for this part A is a $C_1$-$C_6$ saturated aliphatic alcohol, including linear, branched chain, and cyclic alcohols. Non-limiting examples of suitable solvents include alcohols such as methanol, ethanol, isopropanol, and the like, and mixtures thereof.

Part B. The mixture from Part A is combined with a mixture of 4-sulfonamidophenylhydrazine hydrochloride (0.8-1.2 molar equivalents based upon 4-fluoroacetophenone) and aqueous hydrochloric acid (1.1-2.0 molar equivalents based upon 4-fluoroacetophenone) in water (3-9 liters per kilogram of 4-fluoroacetophenone). If required, a suitable solvent may be added such that the total amount of the solvent present in Part B lies within the range of 4-12 liters per kilogram of 4-fluoroacetophenone. The reaction may be heated at temperatures of up to reflux (to effect completion of reaction). Following the reaction period, the mixture is seeded with the crystals of Form I (0.0001% wt/wt based upon 4-fluoroacetophenone or more) at temperatures below 70° C. The solids are isolated by filtration and may be washed and/or reslurried with a suitable solvent. The product may be dried at temperatures up to 80° C. A "suitable solvent" for this part B is a $C_1$-$C_6$ saturated aliphatic alcohol, including linear, branched chain, and cyclic alcohols, and water, and mixtures thereof.

The following procedure describes a method of preparing the crystal Form I of 4-[5-(4-fluorophenyl)-3-(trifluoromethyl)-1H-pyrazol-1-yl]-benzenesulfonamide without isolating the crystal Form II. 2-propanol (70 ml) and ethyl trifluoroacetate (27.15 g, 0.191 moles) are added to a first vessel, followed by a line wash of 2-propanol (10 ml). Next, 25% sodium methoxide in methanol (37.5 g, 0.174 moles) is added to the vessel, followed by a line wash of 2-propanol (10 ml).

Next, 4-fluoroacetophenone (20 g, 0.145 moles) is added followed by a line wash of 2-propanol (10 ml). The contents of vessel are heated to 55° C. and held at that temperature for 2 hours, then cooled to ambient temperature. Water (110 ml), concentrated hydrochloric acid (20.0 g, 0.203 moles), and 4-sulfonamidophenylhydrazine hydrochloride (32.4 g, 0.145 moles) are added to a second vessel, followed by a line wash of water (10 ml). The contents of the first vessel are added to the second vessel, followed by a line wash of 2-propanol (60 ml). The combined contents are heated at 70° C. for 2 hours, then cooled to 55° C. and seeded with 10 mg (0.05% wt/wt relative to 4-fluoroacetophenone) of Form I of 4-[5-(4-fluorophenyl)-3-(trifluoromethyl)-1H-pyrazol-1-yl]-benzenesulfonamide. The contents are held at 55° C. for 6 hours, then cooled to ambient temperature and filtered. The product is washed with 50% aqueous 2-propanol (120 ml) and water (60 ml), then dried under vacuum at 55° C. to give 4-[5-(4-fluorophenyl)-3-(trifluoromethyl)-1H-pyrazol-1-yl]-benzenesulfonamide of the desired Form I polymorph (44.8 g, 80%).

The invention is described in greater detail by the following non-limiting examples.

EXAMPLES

Example 1

Figure 1:
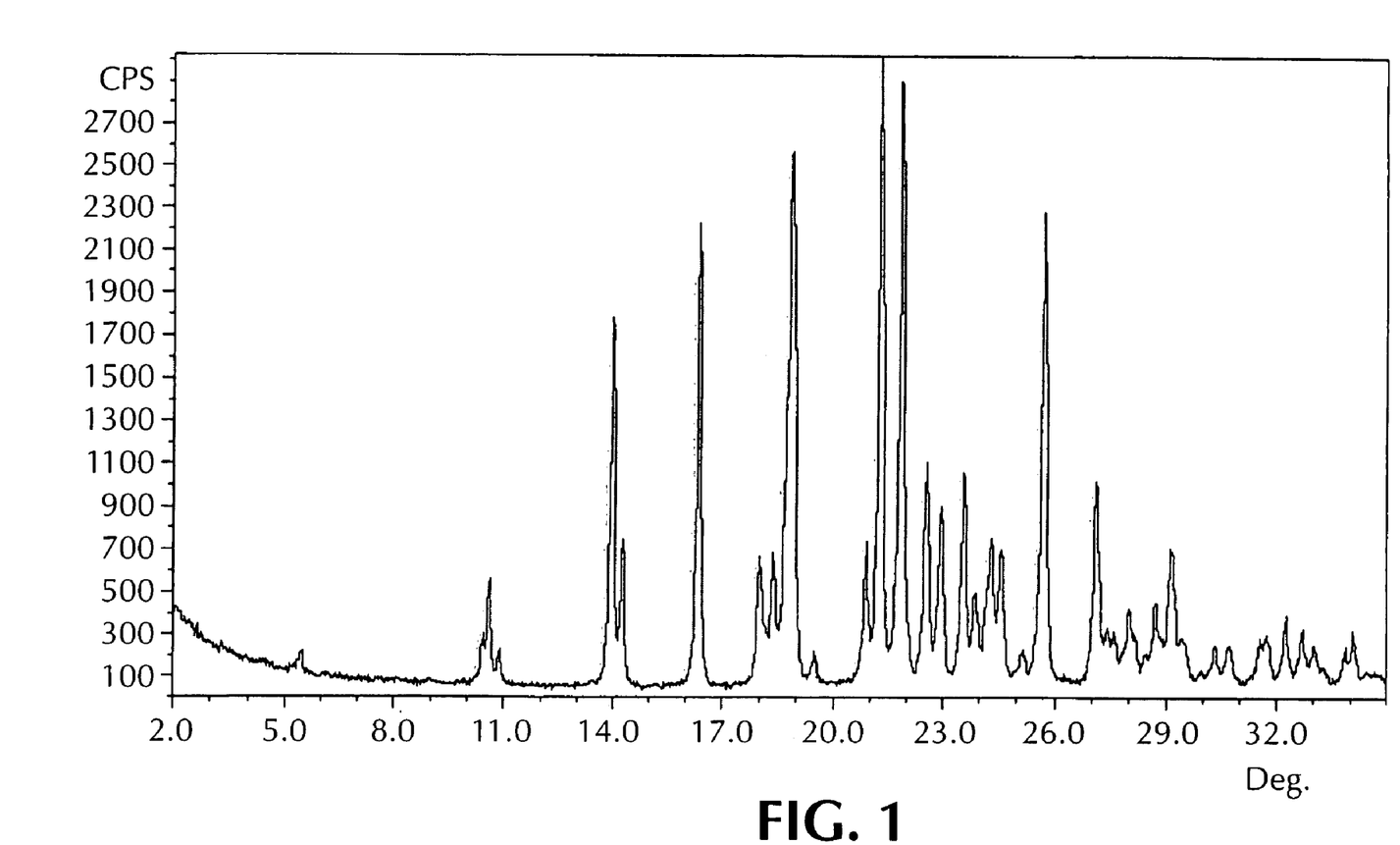
FIG. 1. Presented in FIG. 1 is the experimental powder X-ray diffraction (PXRD) pattern of Form I of 4-[5-(4-fluorophenyl)-3-(trifluoromethyl)-1H-pyrazol-1-yl]-benzenesulfonamide.

De-ionized water, 1 mL, was mixed well with isopropyl alcohol, 1 mL, in a 20 mL glass vial. 4-[5-(4-fluorophenyl)-3-(trifluoromethyl)-1H-pyrazol-1-yl]-benzenesulfonamide, Form II, (258.6 mg) was added to the vial. A magnetic stirring bar was introduced and the vial capped tightly. The suspension was stirred at ~200 rpm for about 30 min. A thick paste-like suspension was observed. The stirring was stopped and the vial was allowed to stand for 3 days. A portion of the suspension was removed and dried on absorbent paper. The powder X-ray pattern of this solid is shown in FIG. 1. The melting point of some isolated crystals observed under a hot stage microscope was 148-152° C. However, this range may not be reproducibly observed because of the transition of Form I to Form II at between 140 to 155° C.

Example 2

380 mg of Form II was suspended in 2 mL of ethanol. Part of the compound was dissolved but some excess solid compound suspended in the solution. The resulting suspension was stirred with a magnetic stirring bar at a temperature from about 20° C. to about 30° C. for 2 weeks. At the end of the period, the solid was filtered and identified by PXRD to be Form I.

Example 3

1.5 g of Form II was added to 2 mL of acetonitrile to afford a suspension. The suspension was stirred with a magnetic stirring bar at a temperature from about 20° C. to about 30° C. for 2 weeks. At the end of the period, the solid was filtered and identified by PXRD to be Form I.

Example 4

0.5 g of Form II was added to 2 mL of methanol+water mixture (1:1, v:v) to afford a suspension. The suspension was stirred with a magnetic stirring bar at a temperature from about 20° C. to about 30° C. for 4 weeks. At the end of the period, the solid was filtered and identified by PXRD to be Form I.

Example 5

81.5 kg 4-[5-(4-fluorophenyl)-3-(trifluoromethyl)-1H-pyrazol-1-yl]-benzenesulfonamide was completely dissolved in 81.5 Kg of ethanol (6 volumes) at 40° C. and filtered while hot. 154 L of water (9 volumes) was added to the solution over a period of 1 hr while the temperature was maintained at 40° C. followed by cooling down to 20° C. The slurry was stirred at 20° C. for 24 hrs, and filtered to provide 4-[5-(4-fluorophenyl)-3-(trifluoromethyl)-1H-pyrazol-1-yl]-benzenesulfonamide as Form I.

Example 6

Powder X-Ray Diffraction

Powder X-ray diffraction was performed using a Scintag X2 Advanced Diffraction System (controlled by Scintag DMS/NT 1.30a and Microsoft Windows NT 4.0 software). The system uses a Copper X-ray source (45 kV and 40 mA) to provide $CuK\alpha_1$ emission of 1.5406 Å and a solid-state Peltier cooled detector. The beam aperture was controlled using tube divergence and anti-scatter slits of 2 and 4 mm and detector anti-scatter and receiving slits of 0.5 and 0.2 mm width. Data were collected from 2 to 35° (two-theta) using a step scan of 0.03°/step with a counting time of one second per step. Scintag round, top loading aluminum sample holders with a 12 mm diameter cavity were utilized for the experiments. Powders were packed into the holder and were gently pressed by a glass slide to ensure coplanarity between the sample surface and the surface of the sample holder.

As will be appreciated by the skilled crystallographer, the relative intensities of the various peaks within Tables given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Tables.

The skilled crystallographer will also appreciate that measurements using a different wavelength will result in different shifts according to the Bragg equation—$n\lambda=2d \sin \theta$.

Such further PXRD patterns generated by use of alternative wavelengths are considered to be alternative representations of the PXRD patterns of the crystalline materials of the present invention and as such are within the scope of the present invention.

For Form I, 2-theta Angles, d spacings and relative intensities were calculated from the single crystal structure using the "Reflex Powder Diffraction" module of Accelrys Materials Studio™ [version 2.2]. Pertinent simulation parameters were in each case:

Wavelength=1.540562 Å (Cu Kα)

Polarisation Factor=0.5

Pseudo-Voigt Profile (U=0.01, V=−0.001, W=0.002)

Figure 2:
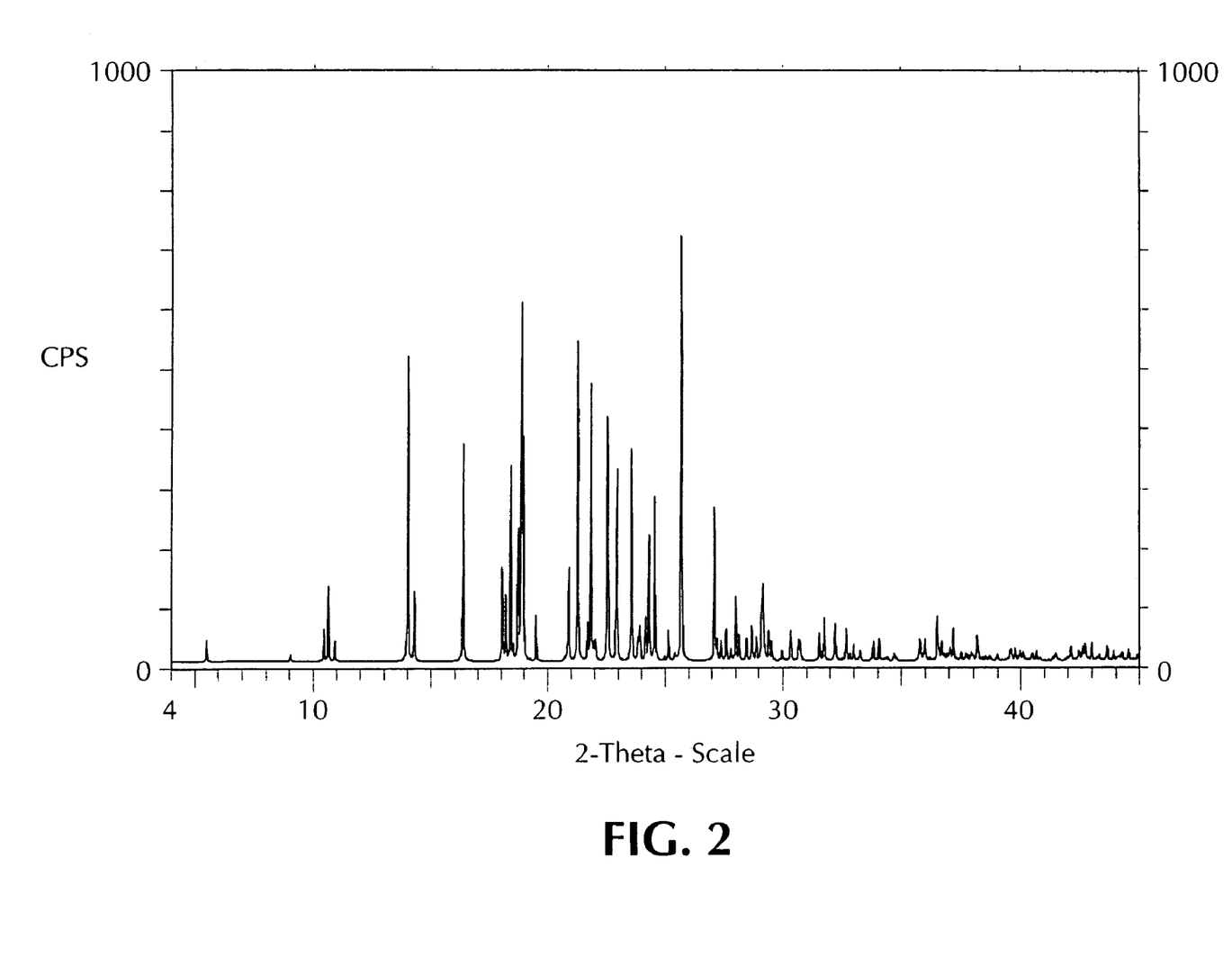
FIG. 2. Presented in FIG. 2 is the calculated powder X-ray diffraction (PXRD) pattern of Form I of 4-[5-(4-fluorophenyl)-3-(trifluoromethyl)-1H-pyrazol-1-yl]-benzenesulfonamide.
Figure 3:
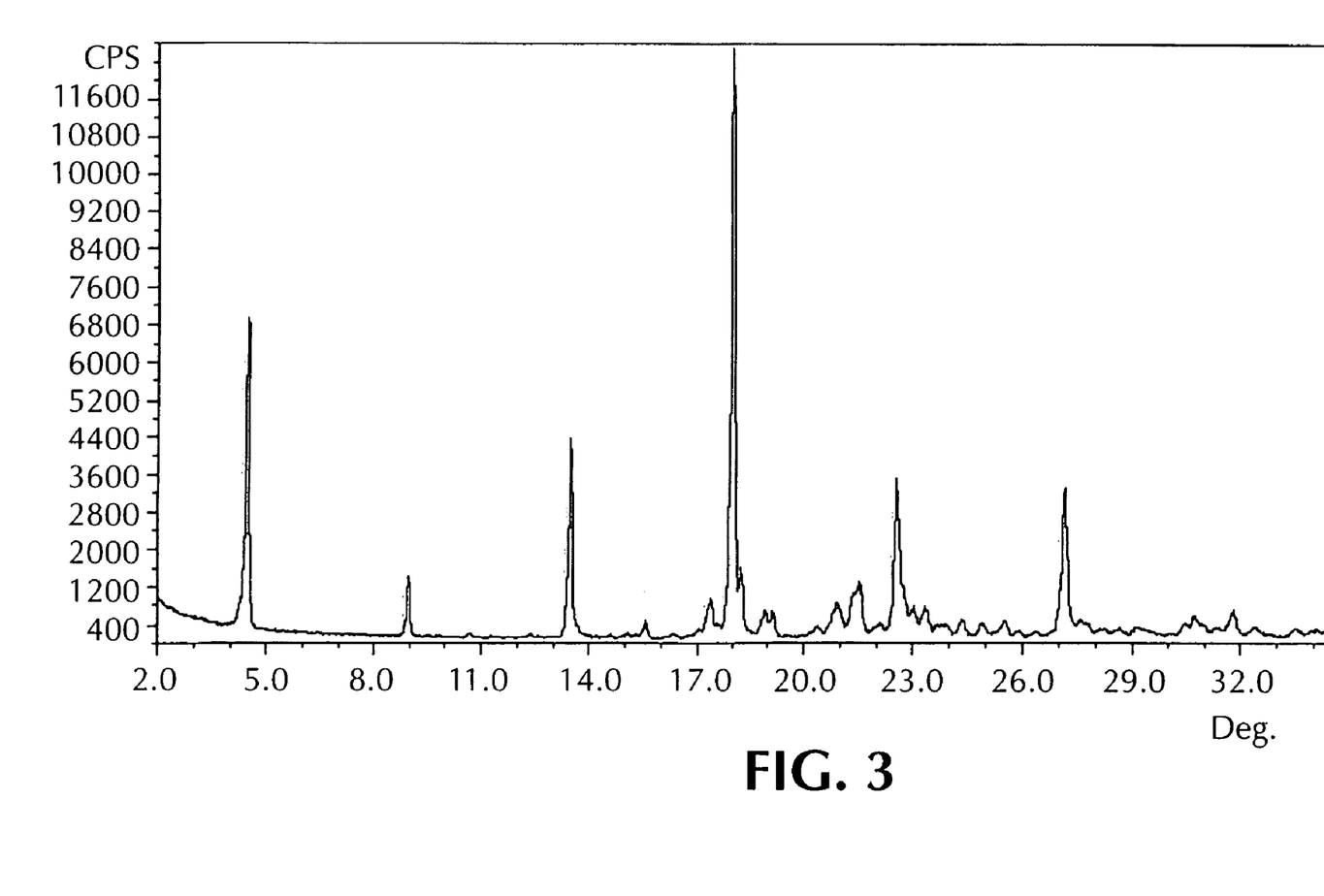
FIG. 3. Presented in FIG. 3 is the powder X-ray diffraction (PXRD) pattern of Form II of 4-[5-(4-fluorophenyl)-3-(trifluoromethyl)-1H-pyrazol-1-yl]-benzenesulfonamide.

The experimental and the calculated PXRD patterns for Form I and the experimental pattern for Form II are given in FIGS. 1, 2 and 3, respectively. The main PXRD peaks of Form I of 4-[5-(4-fluorophenyl)-3-(trifluoromethyl)-1h-pyrazol-1-yl]-benzenesulfonamide are presented in Table 1. The main peaks of Form I of 4-[5-(4-fluorophenyl)-3-(trifluoromethyl)-1h-pyrazol-1-yl]-benzenesulfonamide from the calculated PXRD pattern are presented in Table 2. Form I displays unique diffraction peaks at 14.0, 18.9, 21.3, 21.9, and 25.7 degrees of two theta-angle±0.1 degree.

TABLE 1

PXRD DIFFRACTION PEAKS OF 4-[5-(4-FLUOROPHENYL)-3-(TRIFLUOROMETHYL)-1H-PYRAZOL-1-YL]-BENZENESULFONAMIDE, FORM I

| Angle Two-Theta* (degrees) | Relative Intensity** |
|---|---|
| 10.6 | 14.6 |
| 14.0 | 60.0 |
| 14.3 | 22.2 |
| 16.4 | 74.9 |
| 18.0 | 17.5 |
| 18.4 | 19.3 |
| 18.9 | 80.2 |
| 20.9 | 17.7 |
| 21.3 | 100.0 |
| 21.9 | 96.3 |
| 22.6 | 31.4 |
| 22.9 | 24.0 |
| 23.6 | 28.6 |
| 23.9 | 12.3 |
| 24.4 | 18.6 |
| 24.6 | 19.6 |
| 25.7 | 76.7 |
| 27.1 | 31.9 |
| 28.7 | 11.3 |
| 29.2 | 20.3 |

*±0.1 degree
**The relative intensity for each peak is determined by normalizing its intensity to that of the strongest peak at 21.3° angle as 100

TABLE 2

DIFFRACTION PEAKS OF 4-[5-(4-FLUOROPHENYL)-3-(TRIFLUOROMETHYL)-1H-PYRAZOL-1-YL]-BENZENESULFONAMIDE, FORM I, FROM CALCULATED PXRD PATTERN

| Angle 2-Theta (Degrees)* | Relative Intensity** |
|---|---|
| 10.6 | 18.7 |
| 14.0 | 72.0 |
| 14.3 | 17.8 |
| 16.3 | 51.9 |
| 18.0 | 23.2 |
| 18.1 | 17.2 |
| 18.4 | 46.9 |
| 18.7 | 32.4 |
| 18.9 | 84.6 |
| 18.9 | 54.5 |
| 19.5 | 12.0 |
| 20.9 | 23.1 |
| 21.3 | 75.7 |
| 21.7 | 11.9 |
| 21.8 | 65.7 |
| 22.5 | 58.0 |
| 22.9 | 45.9 |
| 23.5 | 50.5 |
| 24.1 | 12.4 |
| 24.3 | 30.7 |
| 24.5 | 39.5 |
| 25.7 | 100.0 |
| 27.1 | 37.1 |
| 28.0 | 16.3 |
| 29.1 | 16.8 |
| 29.1 | 19.4 |
| 29.4 | 10.1 |
| 31.8 | 11.4 |
| 36.5 | 11.6 |

*±0.1 degree
**The relative intensity for each peak is determined by normalizing its intensity to that of the strongest peak at 25.7° angle as 100

Example 7

Differential Scanning Calorimetry (DSC)

Figure 4:
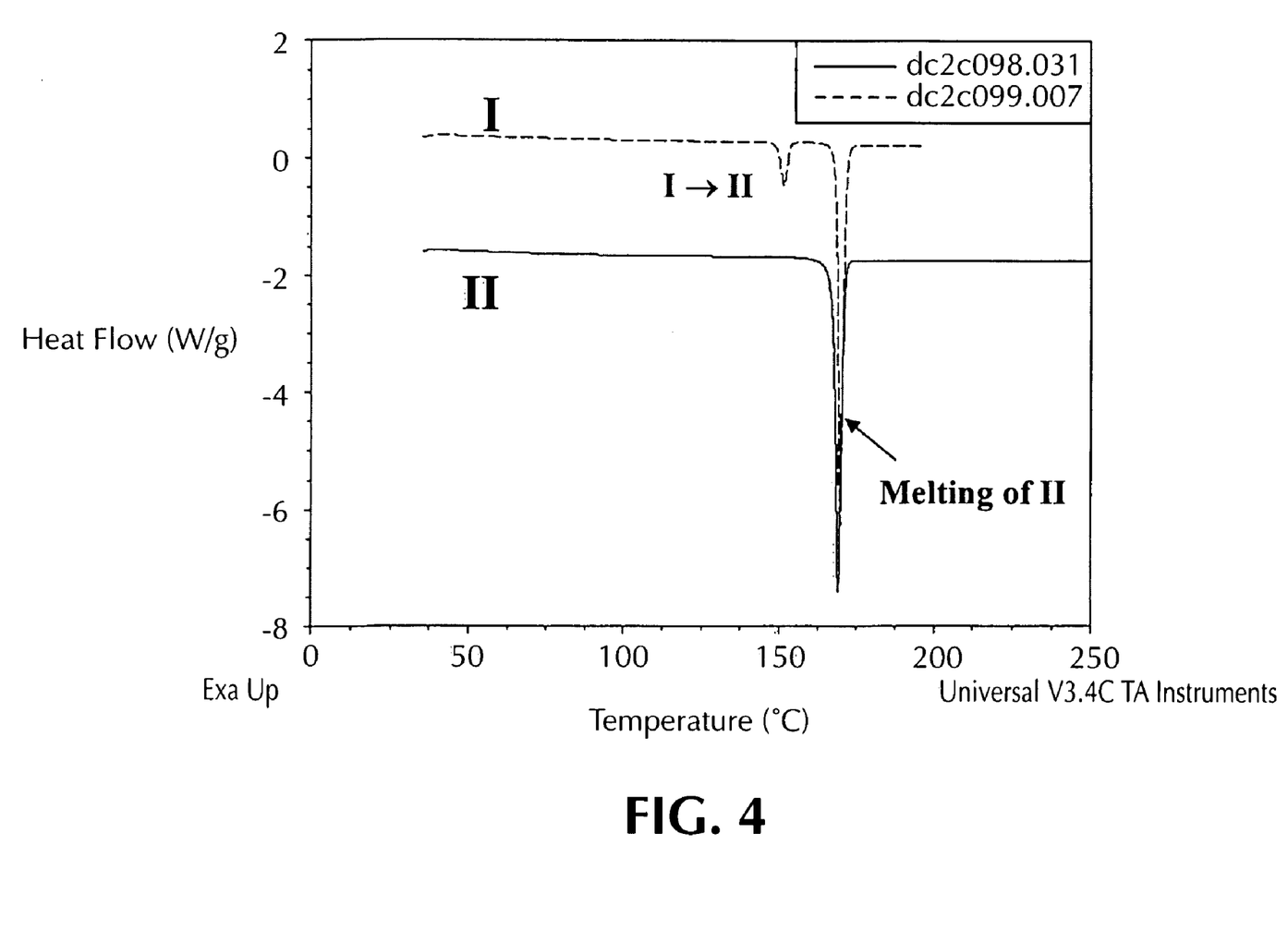
FIG. 4. Presented in FIG. 4, is the differential scanning calorimetry (DSC) data of Forms I and II of 4-[5-(4-fluorophenyl)-3-(trifluoromethyl)-1H-pyrazol-1-yl]-benzenesulfonamide.

Differential scanning calorimetry (DSC) data were obtained using a DSC calorimeter (TA Instruments 2920). Powder (1-5 mg) was packed in an aluminum DSC pan. An aluminum lid was placed on top of the pan and was crimped. The crimped pan was placed in the sample cell along with an empty pan as a reference. Temperatures were increased to 250° C. from 30° C. at a rate of 10° C./min unless otherwise specified. The thermal cell was purged with dry nitrogen at 50 mL/min. The TA Instruments Thermal Solutions™ for NT (version 1.3L) was used for data collection and Universal Analysis™ for NT (version 2.4F) was used for data analysis. As can be seen in FIG. 4, the DSC of Form I shows an endothermal phase transition from Form I to Form II at 140° C. to 155° C.

Example 8

Thermodynamic Relationship Between Forms I and II

In this Example, the transition temperature between Forms I and II is described. Form I and Form II are enantiotropic, which means that one polymorph is stable at temperatures below a transition temperature, $T_t$, but the other polymorph is stable at temperatures above $T_t$. The two solid phases have equal free energies at the transition temperature. Knowledge of the thermodynamic stability relationship is necessary for the selection of suitable crystallization conditions to produce Form I, and for formulation development and commercial manufacturing. It is important to determine $T_t$ for the preparation and processing of bulk drug.

Materials And Methods

Materials. The Form I sample used in this study was 100% pure when tested by HPLC. Form II was prepared by heating Form I to 155° C. for 3 days in a dry oven and cooled to room temperature. This Form II sample was free of chemical degradation when tested by HPLC.

Methods. Suspension crystallization. The relative stability relationship between Forms I and II at a specific temperature was bracketed by suspending a mixture of the two polymorphs in toluene in a closed glass vial that was equilibrated at the temperature of interest. Excess solid of one polymorph was first added to saturate toluene in a glass vial at the chosen temperature. The other polymorph was added at least half an hour later. The suspension was stirred continuously for at least three days. A portion of the suspension was withdrawn and immediately filtered. The filtered solid was analyzed using PXRD to identify the equilibrium solid at that temperature. The equilibrium polymorph is thermodynamically more stable at the specific temperature. By repeating the experiment at different temperatures, the $T_t$ was bracketed.

Results

Suspension Crystallization. The results from suspension crystallization showed that at or about 71.5° C. or greater, a mixture of Forms I and II always converted to Form II, but at or about 71.0° C. or less, Form I was the equilibrium solid phase. Therefore, Form I is thermodynamically more stable at or about 71.0° C. or less, and Form II is more stable at or about 71.5° C. or greater. The $T_t$ must be approximately 70 to about 73° C.

Discussion

It is important to determine the $T_t$ for the preparation and processing of bulk drug. For example, a step comprising crystallization from solution is often involved prior to the final isolation of the bulk drug. If $T_t$ for the desired form lies below the crystallization temperature, it might be difficult to crystallize the drug consistently as a pure phase. Another example is the drying of drug-containing granules after wet-granulation. If the drying temperature is higher than $T_t$ uncontrolled polymorph changes of the drug may occur. The changes in turn may affect the subsequent processing, quality, and performance of final products. The transition temperature, $T_t$, was determined to be approximately 71° C. using suspension crystallization. Because Form I is more stable at temperatures below about 71° C. and becomes metastable with respect to Form II at temperatures above approximately 71° C., Form I crystal should maintain its solid-state stability through the normal range of temperatures for crystallization and storage, as long as the temperature is below about 71° C.

The present invention has been described in detail and by reference to various specific and preferred embodiments and techniques. However, it should be understood that many variations and modifications can be made while remaining within the scope of the invention.

What is claimed is:

1. A crystal form, Form I, of 4-[5-(4-fluorophenyl)-3-(trifluoromethyl)-1H-pyrazol-1-yl]-benzenesulfonamide having a powder X-ray diffraction pattern comprising peaks expressed in degrees (±0.1 degree) of two theta angle of 14.0, 18.9, 21.3, 21.9, and 25.7 obtained using $CuK\alpha_1$ X-ray (wavelength=1.5406 Angstroms).

* * * * *

UNITED STATES PATENT AND TRADEMARK OFFICE
CERTIFICATE OF CORRECTION

PATENT NO. : 7,652,149 B2  Page 1 of 1
APPLICATION NO. : 11/095381
DATED : January 26, 2010
INVENTOR(S) : Changquan Sun It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1050 days.

Signed and Sealed this

Twenty-third Day of November, 2010

David J. Kappos
*Director of the United States Patent and Trademark Office*